United States Patent [19]

Mazzocchi et al.

[11] 4,165,371

[45] Aug. 21, 1979

[54] 1,2,3,4,5,6-HEXAHYDRO-1,6-METHANO-3-BENZAZOCINES

[75] Inventors: Paul H. Mazzocchi, Lanham, Md.; Aline M. Harrison, Dallastown, Pa.

[73] Assignee: Research Corporation, New York, N.Y.

[21] Appl. No.: 716,567

[22] Filed: Aug. 23, 1976

[51] Int. Cl.$^2$ .................... A61K 31/55; C07D 223/32
[52] U.S. Cl. ............................ 424/244; 260/239 BB; 260/340.5; 260/340.7
[58] Field of Search ........... 260/239 BB, 347.7, 340.5, 260/340.7; 424/244

[56] References Cited

U.S. PATENT DOCUMENTS

| | | | |
|---|---|---|---|
| 3,294,817 | 12/1966 | Sallay | 260/239 BB |
| 3,516,987 | 6/1970 | Koo et al. | 260/239 BB |
| 3,686,167 | 8/1972 | Fujimura et al. | 260/239 BB |

OTHER PUBLICATIONS

Takeda et al., "Journal of Med. Chem", vol. 13 #4, 1970, pp. 630–634.

*Primary Examiner*—Donald G. Daus
*Assistant Examiner*—D. B. Springer
*Attorney, Agent, or Firm*—Haight & Huard

[57] ABSTRACT

1,2,3,4,5,6-Hexahydro-1,6-methano-3-benzazocines and derivatives thereof are described together with intermediates and methods for their preparation and pharmaceutical compositions and methods for the use thereof. Representative compounds of this new ring system exhibit useful analgesic activity without either physical dependence liability or narcotic antagonist properties.

17 Claims, No Drawings

1,2,3,4,5,6-HEXAHYDRO-1,6-METHANO-3-BENZAZOCINES

BACKGROUND OF THE INVENTION

This invention was supported in part by Grant No. DMR-72-03021-A04 from the National Science Foundation.

This invention relates to a new series of hexahydrobenzazocine derivatives characterized by a 1,6-methano group.

Analgesic agents have been widely used for thousands of years but many of the potentially most valuable known analgesic agents, e.g., morphine and codeine, exhibit excellent analgesic activity in combination with undesirable addictive properties.

Since in general compounds which show analgesic activity with no physical dependence liability also show narcotic antagonist properties, many analgesics which are also narcotic antagonists have not attained practical utility because of the powerful psychotomimetic effects on the central nervous system which are usually associated with powerful antagonist activity. The compounds of the present invention, however, appear to have a unique combination of properties in being strong analgesics without either physical dependence liability or narcotic antagonist properties.

Hexahydrobenzazocines having mild analgesic properties are described in Canadian Pat. No. 884,889, the contents of which are incorporated by reference herein. A number of compounds belonging to the benzomorphan system have been described by E. L. May and J. G. Murphy in J. Org. Chem. 20:257(1955) and by many subsequent workers, e.g., see A. E. Jacobson, Structure Activity Relationships of Analgesics and their Antagonists in "Handbook of Psychopharmacology," L. L. Iversen, S. D. Iversen and S. H. Snyder, ed., Plenum Publ. Corp. (1976).

The benzomorphans are benzazocines which are bridged by a 2,6-methylene group to form a tricyclic structure from the bicyclic structure of the parent benzazocine compounds. Rogers, et al in J. Med. Chem. 18(10):1036-1038 (1975) notes that the extra ring of the benzomorphans imposes a degree of conformational rigidity not found in the more flexible benzazocines and suggests that this decreased conformational flexibility may be primarily responsible for the increased binding energy between benzomorphans and the opiate receptor as compared to the benzazocines. While not wishing to be bound by the theory of the invention, it is believed that the more symmetrical 1,6-methano group of the compound in accordance with this invention may have a similar effect.

Chang, et al, in J. Med. Chem. 14(10):1011(1971) describe the synthesis of 3-methyl-1,2,3,4,5,6-hexahydro-1,5-methano-3-benzazocines. However, none of the reported compounds showed analgesic activity in the standardized tail pinch test and three compounds caused convulsions in the test animals.

Michne, et al, in J. Med. Chem. 15(12):1278(1972) reported a series of 2,6-methano-3-benzazocine derivatives. The compounds all have an oxygenfunction (keto or hydroxyl group) in the 1-position and exhibited both agonist and antagonish activity.

Mokotoff et al, In J. Hetero. Chem. 7:773(Aug. 1970) described B-norbenzomorphans or 1,5-methano-2,3,4,5-tetrahydro1H-2-benzazepines in which the nitrogen atom of a seven-membered heterocyclic ring is directly attached to a benzylic carbon atom and the heterocyclic ring is fused to a benzene ring. While these compounds lack the "central" carbon atom occurring in almost all of the known analgesics having morphine-like activity, the analgesic activities reported were less active and more toxic than the comparable 6,7-benzomorphans. A comparison of the methoxy analogues of B-norbenzomorphans surprisingly shows more analegesic activity than the corresponding 6,7-benzomorphans; see Jacobson et al., J. Med. Chem. —:7 (1970).

Sallay, U.S. Pat No. 3,819,614 and Takeda et al, J. Med. Chem. —(4):630 (1970) describe 2,7-methano-3H-3-benzazonines in which the benzene ring is fused to a nine-membered heterocyclic ring. In conformity with past experience, these analgesic compounds are characterized by the nitrogen atom in the heterocyclic ring sharing the "central" carbon atom with the benzylic group, in common with most known analgesics having morphine-like activity.

OBJECTS OF THE INVENTION

Accordingly, it is a general object of the present invention to provide a new series of hexahydrobenzazocine derivatives.

Another object of this invention is to provide new compounds having analgesic activity comparable to that of codeine and morphine without physical dependence liability or narcotic antagonist properties.

A further object of this invention is to provide compounds having good analgesic activity with little or no physical dependence liability.

An additional object of this invention is to provide such compounds which possess narcotic antagonist activity.

Still another object of this invention is to provide methods and intermediates for the preparation and methods and compositions for the use of such compounds a still further object of this invention is to provide compounds which are useful as rehabilitation agents and deterents to use of narcotics.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing compounds having in the free base form the general Formula I (a) or (b)

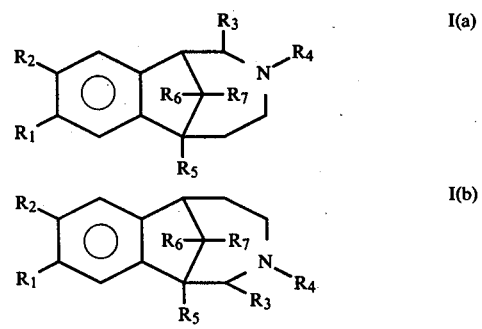

wherein

R$_1$ and R$_2$ are each hydrogen, halogen, alkyl of 1-6 carbon atoms, hydroxy, alkoxy of 1-6 carbon atoms, alkanoyl or alkanoyloxy of 2-7 carbon atoms, amino, mono- or dialkylamino of up to 4 carbon atoms independently in each alkyl group wherein alkyl in each instance is optionally substituted by hydroxy, halogen or amino; or $R_1$ and $R_2$ together form an alkylenedioxy group of 1-4 carbon atoms;

$R_3$ is hydrogen, alkyl of 1-6 carbon atoms, alkoxy of 1-6 carbon atoms, phenyl, or lower alkyl phenyl-lower-alkyl, phenyl-lower-alkyl, each phenyl being optionally substituted by 1-3 hydroxy, halogen, or amino groups;

$R_4$ is hydrogen, alkyl, alkenyl or alkynyl of up to 6 carbon atoms, cycloalkyl, cycloalkylalkyl, cycloalkylalkenyl, cycloalkenyl, cycloalkenylalkyl, hydrocarbon, alicyclic aralkyl or alkaryl alicyclic aralkenyl of up to 9 carbon atoms optionally monsubstituted by amino, morpholino, thienyl, furfuryl, tetrahydrofurfuryl, piperadino, pyrrolidino, hexamethyleneamino, piperazino, alkylpiperazino, alkylamino or dialkylamino each alkyl being of up to 8 carbon atoms, or substituted by carbalkoxy, alkoxy, alkanoyl or alkanoyloxy of 1-4 carbon atoms or by 1-3 of halogen, cyano or hydroxyl; or $R_4$ is aromatic or non-aromatic heterocyclic alkyl optionally substituted by 1-3 of hydroxy, halogen or amino;

$R_5$ is hydrogen, alkyl of 1-6 carbon atoms, hydroxy, alkoxy, alkanoyl or alkanoyloxy of 1-6 carbon atoms, hydrocarbon aryl hydrocarbon alkaryl or alicyclic aralkyl of 6-10 ring carbon atoms and 1-4 alkyl carbon atoms optionally substituted by 1-3 hydroxy, halogen or amino groups; and One of $R_6$ and $R_7$ is hydrogen, hydroxy, alkyl of 1-4 carbon atoms or alkoxy of 1-4 carbon atoms and the other of $R_6$ and $R_7$ is hydrogen, alkyl of 1-6 carbon atoms, hydroxy, alkoxy of 1-6 carbon atoms, aryl hydrocaron alkaryl alicyclic aralkyl of 6-10 ring carbon atoms and 1-4 alkyl carbon atoms, each of which is optionally substituted by 1-3 hydroxy, halogen or amino groups.

DETAILED DISCUSSION

Preferred compounds of the present invention are those of the above general formulae meeting one or more of the following definitions:

(a) Compounds in which $R_1$ is hydroxy, alkoxy, alkanoyl, alkanoyloxy, preferably of 1-4 carbon atoms and especially hydroxy and acetyl;

(b) Compounds in which $R_2$ is hydrogen;

(c) Compounds in which $R_3$ is hydrogen, alkyl or alkoxy, preferably of 1-3 carbon atoms;

(d) Compounds in which $R_3$ is hydrogen;

(e) Compounds in which $R_4$ is hydrogen, alkyl, alkenyl, cycloalkyl, cycloalkylalkyl, cycloalkylalkenyl, cycloalkenyl, cycloalkenylalkyl, phenyl, alkylphenyl, phenylalkyl, alkyphenylalkyl, or an aromatic or non-aromatic heterocyclic alkyl optionally substituted by hyroxy, halogen or amino;

(f) Compounds in which $R_4$ is methyl, allyl, dimethylallyl, 2-phenylethyl, cyclobutylmethyl or cyclopropylmethyl;

(g) Compounds in which $R_4$ is (2-tetrahydrofurfuryl)-methyl or (2-furfuryl)methyl;

(h) Compounds in which $R_5$ is hydrogen, alkyl, alkoxy, alkanoyl, alkanoyloxy or a carboalkoxy ester, preferably of 1-4 carbon atoms, phenyl or benzyl;

(i) Compounds in which $R_5$ is hydrogen, methyl, phenyl or acetoxy, especially hydrogen or methyl;

(j) Compounds in which one of $R_6$ and $R_7$ is hydrogen and the other of $R_6$ and $R_7$ is hydrogen, hydroxy, alkyl or alkoxy, preferably of 1-3 carbon atoms; especially when $R_7$ = OH and/or $R_6$ = $CH_3$;

(k) Compounds in which $R_6$ or $R_7$ is phenyl, tolyl or benzyl;

(l) Compounds in which any halogen present is present as chlorine, bromine or trifluoromethyl;

(m) Compounds in which each of $R_1$, $R_2$, $R_3$, $R_4$, $R_5$, $R_6$ and $R_7$ meet one or more of the above preferred definitions;

(n) Compounds in which $R_6$ or $R_7$ = H while the other position and $R_5$ have alkyl groups of 2-5 total carbon atoms for both positions; and (o) Compounds in which $R_6$ or $R_7$ = H while the other position and $R_5$ and $R_4$ have alkyl groups, the total number of carbon atoms at the three alkylated positions being 3-7.

Compounds of the present invention, in addition to thse shown in the following Examples, include but are not limited to the following preferred compounds of the structure shown in Formula I(a) wherein $R_2$, $R_3$ and $R_7(\beta)$ are each hydrogen;

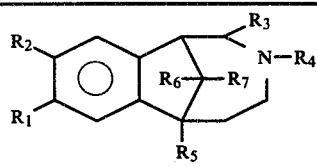

| COMPOUND NO. | $R_1$ | $R_4$ | $R_5$ | $R_{6(\alpha)}$ |
|---|---|---|---|---|
| 1 | —H | —H | —H | —H |
| 2 | —H | —$CH_3$ | —H | —H |
| 3 | —H | —$CH_2CH_2C_6H_5$ | —H | —H |
| 4 | —H | —$CH_2CH_2CH_3$ | —H | —H |
| 5 | —H | —$CH_2$—▷ | —H | —H |
| 6 | —H | —$HC_2$—CH=$CH_2$ | —H | —H |
| 7 | —H | —$CH_2$—CH=C$\overset{CH_3}{\underset{CH_3}{}}$ | —H | —H |
| 8 | —OH | —H | —H | —H |
| 9 | —OH | —$CH_3$ | —H | —H |
| 10 | —OH | —$CH_2CH_2C_6H_5$ | —H | —H |
| 11 | —OH | —$CH_2CH_2CH_3$ | —H | —H |

-continued

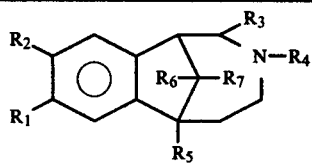

| COMPOUND NO. | R₁ | R₄ | R₅ | R₆(α) |
|---|---|---|---|---|
| 12 | —OH | —CH₂—△ | —H | —H |
| 13 | —OH | —CH₂—□ | —H | —H |
| 14 | —OH | —CH₂—CH=CH₂ | —H | —H |
| 15 | —OH | —CH₂—CH=C(CH₃)CH₃ | —H | —H |
| 16 | —OH | —H | —CH₃ | —H |
| 17 | —OH | —CH₃ | —CH₃ | —H |
| 18 | —OH | —CH₂CH₂C₆H₅ | —CH₃ | —H |
| 19 | —OH | —CH₂CH₂CH₃ | —CH₃ | —H |
| 20 | —OH | —CH₂—△ | —CH₃ | —H |
| 21 | —OH | —CH₂—CH=CH₂ | —CH₃ | —H |
| 22 | —OH | —CH₂—CH=C(CH₃)CH₃ | —CH₃ | —H |
| 23 | —OH | —H | —CH₃ | —CH₃ |
| 24 | —OH | —CH₃ | —CH₃ | —CH₃ |
| 25 | —OH | —CH₂CH₂C₆H₅ | —CH₃ | —CH₃ |
| 26 | —OH | —CH₂—△ | —CH₃ | —CH₃ |
| 27 | —OH | —CH₂—CH=C(CH₃)CH₃ | —CH₃ | —CH₃ |
| 28 | —OH | —H | —H | —CH₃ |
| 29 | —OH | —CH₃ | —H | —CH₃ |
| 30 | —OH | —CH₂CH₂C₆H₅ | —H | —CH₃ |
| 31 | —OH | —CH₂—△ | —H | —CH₃ |
| 32 | —OH | —CH₂—CH=C(CH₃)CH₃ | —H | —CH₃ |
| 33 | CH₃C(O)—O— | —H | —H | —H |
| 34 | CH₃C(O)—O— | —CH₃ | —H | —H |
| 35 | CH₃C(O)—O— | —CH₂CH₂C₆H₅ | —H | —H |
| 36 | CH₃C(O)—O— | —CH₂—△ | —H | —H |
| 37 | CH₃C(O)—O— | —CH₂CH=C(CH₃)CH₃ | —H | —H |
| 38 | CH₃C(O)—O— | —H | —CH₃ | —H |
| 39 | CH₃C(O)—O— | —CH₃ | —CH₃ | —H |
| 40 | CH₃C(O)—O— | —CH₂CH₂C₆H₅ | —CH₃ | —H |
| 41 | CH₃C(O)—O— | —CH₂—△ | —CH₃ | —H |
| 42 | CH₃C(O)—O— | —CH₂—CH=C(CH₃)CH₃ | —CH₃ | —H |

-continued

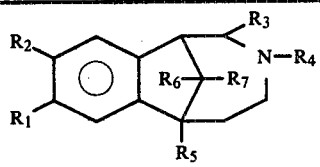

| COMPOUND NO. | R₁ | R₄ | R₅ | R₆(α) |
|---|---|---|---|---|
| 43 | CH₃C(=O)O— | —H | —CH₃ | —CH₃ |
| 44 | CH₃C(=O)O— | —CH₃ | —CH₃ | —CH₃ |
| 45 | CH₃C(=O)O— | —CH₂CH₂C₆H₅ | —CH₃ | —CH₃ |
| 46 | CH₃C(=O)O— | —CH₂-cyclopropyl | —CH₃ | —CH₃ |
| 47 | CH₃C(=O)O— | —CH₂—CH=C(CH₃)CH₃ | —CH₃ | —CH₃ |
| 48 | CH₃C(=O)O— | —H | —H | —CH₃ |
| 49 | CH₃C(=O)O— | —CH₃ | —H | —CH₃ |
| 50 | CH₃C(=O)O— | —CH₂CH₂C₆H₅ | —H | —CH₃ |
| 51 | CH₃C(=O)O— | —CH₂-cyclopropyl | —H | —CH₃ |
| 52 | CH₃C(=O)O— | —CH₂CH=C(CH₃)CH₃ | —H | —CH₃ |
| 53 | —OH | —H | —C₆H₅ | —CH₃ |
| 54 | —OH | —CH₃ | —C₆H₅ | —CH₃ |
| 55 | —OH | —CH₂CH₂C₆H₅ | —C₆H₅ | —CH₃ |
| 56 | —OH | —CH₂-cyclopropyl | —C₆H₅ | —CH₃ |
| 57 | —OH | —CH₂CH=C(CH₃)CH₃ | —C₆H₅ | —CH₃ |
| 58 | —OH | —H | —C₆H₅ | —H |
| 59 | —OH | —CH₃ | —C₆H₅ | —H |
| 60 | —OH | —CH₂CH₂C₆H₅ | —C₆H₅ | —H |
| 61 | —OH | —CH₂-cyclopropyl | —C₆H₅ | —H |
| 62 | —OH | —CH₂CH=C(CH₃)CH₃ | —C₆H₅ | —H |
| 63 | —H | —CH₂-(tetrahydrofuran-2-yl) | —H | —H |
| 64 | —OH | —CH₂-(tetrahydrofuran-2-yl) | —H | —H |
| 65 | CH₃C(=O)O— | —CH₂-(tetrahydrofuran-2-yl) | —H | —H |
| 66 | —H | —CH₂-(tetrahydrofuran-2-yl) | —CH₃ | —H |
| 67 | —OH | —CH₂-(tetrahydrofuran-2-yl) | —CH₃ | —H |
| 68 | CH₃C(=O)O— | —CH₂-(tetrahydrofuran-2-yl) | —CH₃ | —H |

-continued

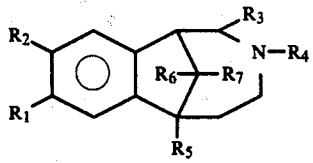

| COMPOUND NO. | $R_1$ | $R_4$ | $R_5$ | $R_{6(a)}$ |
|---|---|---|---|---|
| 69 | —OH | —CH$_2$-[tetrahydrofuranyl] | C$_6$H$_5$— | —H |

Compounds of Formula I wherein $R_4$ is hydrogen can be prepared from starting materials which themselves are known or can be prepared by methods analogous to those known in the art. For example, compounds of Formula I wherein $R_4$ is hydrogen can be prepared from polycyclic β-lactams of Formula II

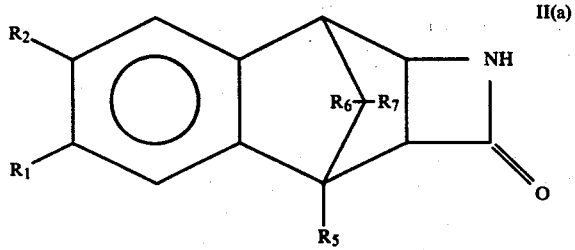

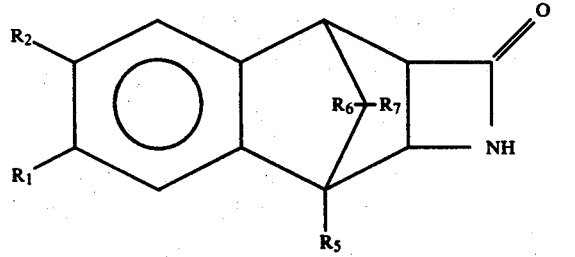

wherein $R_1$, $R_2$, $R_5$, $R_6$ and $R_7$ have the above-indicated values which themselves can be prepared analogously to the procedure described in J.A.C.S. 95(6):1968 (March 21, 1973) from the corresponding benzonorbornadienes by reaction with chlorosulfonyl isocyanate to form the N-chlorosufonyl β-lactam which is then reduced, e.g., with sodium sulfite, to form the polycyclic β-lactam of Formula II.

The relative yield of isomers II(a) and II(b) can be modified by the use of a benzonorbornadiene having a known o- or p-directing group theron at the 6-position (corresponding to $R_5$ in the above formulae), e.g., a methyl or preferably methoxy substituent leads to higher yield of the isomer II(a) with the carboxyl group closest to the methoxy group while a fluorine substituent at $R_5$ has the opposite effect and leads to higher yields of the isomer II(b).

The polycyclic β-lactams of Formula II are etherified at the ring carbon atom adjacent to both the ring nitrogen atom and the bridiging 1,6-methano group, e.g., by photochemical ring expansion analogous to the procedure described in J.A.C.S. 95(6):1968(March 21, 1973) to form a precursor lactam ether of Formula III

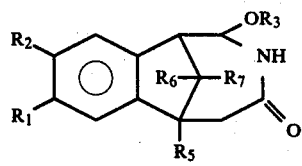

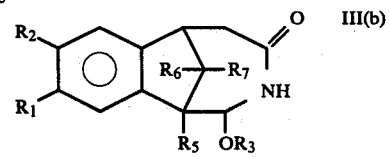

The lactam ether of Formula III can be reduced to the corresponding amine of Formula I using a variety of known lactam reducing methods, e.g., procedures analogous to those described in J. Hetero. Chem. 7:773(1970); J. Med. Chem. 13(1): 7 (1970); J. Med. chem. 18(12):1266(1975); etc.

Compounds of Formula I wherein $R_4$ is other than hydrogen can then be prepared by substitution of the secondary amine hydrogen atom with the desire radical using methods well known in the art for analogous N-substitution of benzomorphans, benazocines and related compounds, e.g., see Canadian Pat. No. 884,889 and U.S. Pat. No. 3,856,795.

Compounds of this invention which contain a center of asymmetry ordinarily are obtained in the racemic form. The racemates can be separated into their optical antipodes in accordance with a plurality of known methods described in the literature; chemical separation is preferred. According to this procedure, diastereomers are formed from the racemic mixture by reaction with a optically active auxiliary agent. Thus, an optically active base can be reacted with a carboxyl group, or an optically active acid with the amino group, of a compound of this invention. For example, diastereomeric salts of basic compounds can be formed with optically active acids, e.g., (+)- and (−) -tartaric acid, dibenzoyl-(+)- and -(−)-tartaric acid, diacetyl-(+)- and -(−)-tartaric acid, camphoric acid, β-camphorsulfonic acid, (+)- and (−)-mandelic acid, (+)- and (−)-malic acid, (+)- and (−)-2-phenylbutyric acid, (+)- and (−)-dinitrodiphenic acid, or (+)- and (−)-lactic acid. In a smilar manner, ester diastereomers can be produced by the esterification of compounds cntaning a free carboxyl group with optically active alcohols, e.g. borneol, menthol or 2-octanol. The thus-obtained mixtures of diastereomeric salts and/or esters can be separated by selective crystallization. The desired optically active compounds can be produced by hydrolytic separation of the isolated diastereomeric compound.

A basic compound of Formula I can be converted nto the associated acid addition salt with the use of an acid. For this reaction, suitable acids are those yielding physiologically acceptable salts. Suitable organic and inorganic acids are well known in the art and include but are not limited to aliphatic, alicyclic, araliphatic, aromatic and heterocyclic, mono- or polybasic carboxylic or sulfonic acids, e.g., formic acid, acetic acid, propionic acid, pivalic acid, diethylacetic acid, oxalic acid, malonic acid, succinic acid, pimelic acid, fumaric acid, maleic acid, lactic acid, tataric acid, malic acid, aminocarboxylic acids, sulfamic acid, benzoic acid, salicyclic acid, phenylpropionic acid, citric acid, gluconic acid, ascorbic acid, nicotinic acid, isonicotinic acid, methanesulfonic acid, ethanedisulfonic acid, $\alpha$-hydroxyethanesulfonic acid, p-toluenesulfonic acid, naphthalene-mono- and -disulfonic acids, sulfuric acid, nitric acid, hydrohalic acids, e.g., hydrochloric acid and hydrobromic acid, and phosphoric acids, e.g., orthophosphoric acid.

Due to their analgesic activity, the compounds of Formula I (a) and I (b) are useful agents in human and veterinary medicine. They can be administered, for example, in substantially the same manner as the known analgesic compound pentazocine.

The compounds of this invention can be employed in mixture with conventional excipients, i.e., pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 1–100 mg. of a pharmaceutical carrier per each unit dosage and the amount of active agent of the invention per unit dosage is about 10 to 60 mg.

For topical application, these are employed as nonsprayable forms, viscous to semi-solid or solid forms comprising a carrier indigenous to topical application and having a dynamic viscosity preferably greater than water. Suitable formulations include but are not limited to solutions, suspensions, emulsions, creams, ointments, powders, liniments, salves, aerosols, etc. which are, if desired, sterilized or mixed with auxiliary agents. e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon. Usually, the active compounds of the invention are incorporated in topical formulations in a concentration of about 1 to 10 weight percent.

The compounds of this invention are generally administered to animals, including but not limited to mammals, e.g., laboratory animals, livestock, household pets and humans. An analogesically effective dialy dosage of the active compounds as administered intraveneously to monkeys generally comprises about 1 to 500, preferably 10 to 100 mg/kg, together with 1-5,000 mg. of pharmaceutically acceptable carrier. The dose can be administered singly or preferably as divided dosages throughout the day.

It will be appreciated that the actual preferred amounts of active compounds used will vary according to the specific compound being utilized, the particular compositions formulated, the mode of application, and the particular situs and organism being treated. Optimal application rates for a given set of conditions can be ascertained by those skilled in the art using conventional dosage determination tests in view of the above guidelines.

The compounds of Formulae II and III are useful as intermediates in the production of analgesic compounds of Formula I by the methods described herein.

So that the activity and characteristic structures of the compounds of Formula I are predominantly that of a 1,2,3,4,5,6-hexahydro-1,6-methano-3-benzazocine, the sum of the molecular weights of the substituents therein is generally less than about 200, preferably less than about 150, and these substituents preferably contain a total of not more than 20 carbon atoms and not more than 5 heteroatoms. Preferred compounds of Formula I are those which show useful analgesic activity, little or no physical dependence liability and little or no narcotic antogonist activity.

Aliphatic or cycloaliphatic is preferably of up to 6 carbon atoms, e.g., alkyl, alkenyl, cycloalkyl or cycloalkenyl. Suitable alkyl groups include but are not limited to methyl, ethyl, n-propyl, ispropyl, n-butyl, isobutyl, sec.-butyl and tert.-butyl. Suitable alkenyl groups include but are not limited to vinyl, 2,2-dimethylvinyl, allyl, dimethylallyl, 1-propenyl, 1-butenyl, 2-butenyl, 3-methyl-2-butenyl, 1-pentenyl and 2-pentenyl. Suitable cycloalkyl groups include but are not limited to cyclopropyl, cyclobutyl, cyclopentyl and cyclohexyl optionally substituted, e.g., by alkyl or alkenyl of up to 4 carbon atoms to form cycloalkylalkyl or cycloalkylalkenyl, e.g., cyclopropylmethyl. Suitable cycloalkenyl groups include but are not limited to cyclobutenyl, cyclopentenyl and cyclohexenyl optionally substituted, e.g., by alkyl or alkeny of up to 4 carbon atoms to form cycloalkenyl alkyl or cycloalkenyl alkenyl, e.g., cyclobutenylethyl.

Hydrocarbon aryl is preferably phenyl, naphthyl or substituted phenyl; hydrocarbon alkaryl is preferably alkylphenyl or substituted alkyphenyl, e.g., tolyl; and alicyclic aralkyl is preferably phenylalkyl or substituted phenalkyl of 1 to 4 carbon atoms in the alkyl substituent, e.g., benzyl or phenethyl. Aralkenyl is preferably phenylalkenyl of 2 to 6 carbon atoms in the alkenyl substituent, e.g., phenallyl.

Heterocyclic preferably contains 3 to 6 ring atoms including 1 to 3, preferably 1 or 2 hetero atoms, e.g., nitrogen, sulfur or oxygen, preferably morpholino, tetrahydrofurfuryl, piperidino, pyrrolidino, hexamethyleneimino or piperazino, each of which is optionally substituted, e.g., by alkyl of 1–4 carbon atoms.

Alkylenedioxy is preferably of 1–4 carbon atoms, e.g., methylendioxy, ethylenedioxy, etc.

Hydroxy can be free, etherified by an aliphatic, cycloaliphatic, alicyclic or heterocyclic aryl substituent as defined herein, or esterified by aliphatic, cycloaliphatic, aryl or heterocyclic sulfonic or preferably carboxylic acid Preferred aminoalkyl esters are those wherein amino is saturated heterocyclic amino, e.g., piperazino, N-methylpiperazino, morpholino or pyrrolidino or especially alkylamino.

Suitable amines include but are not limited to monoalkylamines, e.g., methylamine, ethylamine, n-propylamine, isopropylamine, n-butylamine and isobutylamine; dialkylamines, e.g., dimethylamine, methylethylamine, diethylamine, di-n-propylamine, diisopropylamine, di-n-butylamine and diisobutylamine; aryl- and aralkylamines, e.g., aniline and benzylamine; hydroxyalkylamines, e.g., ethanolamine and diethanolamine; cyclic amines, e.g., pyrrolidine, piperidine, morpholine, thiomorpholine, piperazine and N-alkylpiperazines such as N-methyl- or N-ethylpiperazine and N-hydroxyalkylpiperazines, e.g., N-2-hydroxyethylpiperazine.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight. The values obtained in elemental analyses are within commonly accepted limits of error.

EXAMPLE 1

Preparation of
2-Methoxy-2,3,5,6-tetrahydro-1,6-methano-3-benzazocin-4(1H)-one

The known exo-3-aza-4-ketobenzotricyclo[4.2.1]non-7-ene (6.00 g, 0.032 mol) was dissolved in 2 l. of methanol and irradiated under nitrogen with a 450 watt Hanovia Type L lamp for approximately 24 hours (with stirring). Solvent was removed under reduced pressure, and the semisolid residue triturated with 25 ml of acetone, giving an off-white powder. Two recyrstallizations from acetone gave material melting at 205°–207°, m/e 217 (M+). The infrared and NMR spectra were identical to those previously reported for this compound in J.A.C.S. 95 (6):1968 (1973) and the references cited therein.

EXAMPLE 2

Preparation of
1,2,3,4,5,6-hexahydro-1,6-methano-3-benzazocine hydrochloride

To a 1 l. flask equipped with an addition funnel, condenser and nitrogen inlet (all pre-dried) were added 250 ml of tetrahydrofuran (freshly distilled from calcium hydride) and 6.17 g (0.163 mol) of lithium aluminum hydride. A solution of 5.7g (0.0263 mol) of 2-methoxy-2,3,5,6-tetrahydro-1,6-methano-3-benzazocin-4(1H)-one in 350 ml tetrahydrofuran (dried) was rapidly added with stirring, after which the mixture was heated at reflux for seven days. The mixture was cooled and hydrolysis accomplished by successive additions of 6.2 ml water in 24 ml tetrahydrofuran, 6.2 ml 15% sodium hydroxide, and 19 ml of water in 75 ml of tetrahydrofuran. Stirring was continued for 20–30 minutes and the mixture filtered by suction.

Approximately 400 ml of benzene was added to the filtrate and the mixture concentrated in vacuo. The residue was distilled (90°–110° bath temperature, 0.1 mm) to give 1,2,3,4,5,6-hexahydro-1,6-methano-3-benzazocine (3.85g, 86%). IR(neat) 3270 broad (s) (N-H stretch), 1140 (s) 1020 (s), 760 (s), 740 (s) cm$^{-1}$.

The free amine was dissolved in ether and hydrogen chloride gas passed through the solution, giving a white flocculent precipitate which was filtered and recrystallized from methanol-acetone (1:3).m.p. 272°–275° (d);

IR (CHCl$_3$) 2850-2650 broad (s), 1590 (m), 1450 (m) cm$^{-1}$;

NMR(D$_2$O) δ 1.6–3.8 (10 H, m, aliphatic), 7.4 (4H, s, aromatic).

Anal. for C$_{12}$H$_{16}$NCl (209.7): Calculated: C, 68.72; H, 7.69; N, 6.68. Found: C, 68.95; H, 7.74; N, 6.59.

EXAMPLE 3

Preparation of
3-methyl-1,2,3,4,5,6-hexahydro-1,6-methano-3-benzazocine hydrochloride To a 10 ml round bottom flask were added 1.50 g (0.00867 ) of 1,2,3,4,5,6-hexahydro-1,6-methano-3-benzazocine, 2ml of formic acid and 2 ml of 40% formaldehyde. The mixture was heated at 95–105° for 3 hours, cooled, 60 ml of 15% sodium hydroxide added, and the aqueous layer extracted with four 60-ml portions of methylene chloride. The combined extracts were concentrated in vacuo in the presence of benzene to remove water. The residue, 1.55 g (0.00829 mol), was distilled (90°–115° bath temperature, 0.1 mm) to give colorless 3-methyl-1,2,3,4,5,6-hexahydro-1,6-methano-3-benzazocine (1.1g, 68% yield). The amine was dissolved in ether and hydrogen chloride gas passed into the solution. The white precipitate obtained was filtered and recrystallized from acetone-ether: m.p. 215°–216° (d); m/e 187 (M+-HCl).

IR (CHCl$_3$) 2670 (s), 2550 (s), 2440 (s) 1460 (m), 1410 (m), 1240-1200 broad (m) cm$^{-1}$.

NMR(D$_2$O)δ1.6–3.9 (15H, m, aliphatic), 7.45 (4H, s, aromatic).

Anal. for C$_{13}$H$_{18}$NCl (223.8): Calculated: C, 69.70; H, 8.10; N, 6.26. Found: C, 69.90; H, 8.30; N 6.21.

EXAMPLE 4

Preparation of
3-cyclopropylcarbonyl-1,2,3,4,5,6-hexahydro-1,6-methano-3-benzazocine To 2.00 g (0.0116 mol) of 1,2,3,4,5,6-hexahydro-1,6-methano-3-benzazocine in 29 ml of methanol were added 4.3 ml of water and 2.86 g (0.0207 mol) of potassium carbonate. The mixture was stirred in an ice bath while 2.26 g (0.0216 mol) of cyclopropylcarbonyl chloride was added dropwise and stirring continued for an additional three hours.

The solvent was removed in vacuo from the crude reaction mixture and the residue treated with 60 ml water, 40 ml benzene and 20 ml 1-butanol. The organic layer was separated and washed with two 60-ml portions of 3N hydrochloric acid and two 60-ml portions of water, concentrated in vacuo, and 100 ml benzene and ca. 0.5 g sodium sulfate were added. The resultant mixture was filtered and concentrated in vacuo, affording 2.1g of residue which was distilled (220°–240° bath temperature, 0.1mm) to give 1.6g (57%) of colorless product: m/e 241 (M+);

IR (CCL$_4$) 1640 (s) (amide C=O), 1475 (m), 1455 (m), 1430 (m) cm$^{-1}$;

NMR(CDCl$_3$) δ0.2–1.20 (4H, m, cyclopropyl), 0.65–4.8 (11H, m, aliphatic) 7.2 (4H, s, aromatic).

Anal. for C$_{16}$H$_{19}$NO (241.3): Calculated: C, 79.63; H, 7.94; N, 5.80. Found: C, 79.38; H, 7.99; N, 5.67.

EXAMPLE 5

Preparation of
3-cyclopropylmethyl-1,2,3,4,5,6-hexahydro-1,6-methano-3-benzazocine hydrochloride Analogously to the procedure of Example 4, to a slurry of 0.69 g (0.0182 mol) lithium aluminum hydride in 25 ml dry tetrahydrofuran (under nitrogen), a solution of 1.39g (0.00576 mol) of 3-cyclopropylcarbonyl-1,2,3,4,5,6-hexahydro-1,6-methano-3-benzazocine in 14 ml dry tetrahydrofuran was added dropwise. The reaction mixture was heated and maintained at reflux for three hours, cooled and hydrolyzed by addition of a solution of 1.3 ml water in 25 ml tetrahydrofuran. The mixture was filtered, 100 ml of benzene added to the filtrate and this solution was concentrated in vacuo. The residue was distilled (120°–160° bath temperature, 0.1 mm) to give 0.89 g (68%) of the amine which was dissolved in ether. Hydrogen chloride was passed into the resultant solution to give a copious white precipitate. The amine hydrochloride was recrystallized from methanol-ether: m.p. 228°–230° (d); m/e 227 (M+-HCl);

IR (CH$_2$CL$_2$) 2500–2300 broad (m), 1480 (m), 1460 (m), 1420 (m) cm$^{-1}$;

NMR(D$_2$O) δ0.2–1.2 (5H, m, cyclopropyl), 1.6–4.0 (12H, m, aliphatic), 7.3 (4H, m, aromatic).

Anal. for C$_{16}$H$_{22}$NCl (263.8): Calculated: C, 72.84; H, 8.41; N, 5.31. Found: C, 73.12; H, 8.68; N, 5.15.

EXAMPLE 6

Preparation of
3-(2-phenylethyl)-1,2,3,4,5,6-hexahydro-1,6-methano-3-benzazocine hydrochloride To 1.0 g (0.0058 mol) of 1,2,3,4,5,6-hexahydro-1,6-methano-3-benzazocine and 1.97 g (0.0143 mol) of potassium carbonate in 25 ml of dimethylformamide (freshly distilled from calcium hydride) was added 1.11 g (0.0060 mol) of 2-phenylethyl bromide and the mixture heated at 90°–110° overnight with stirring. The mixture was cooled, dimethylformamide was removed in vacuo, and 65 ml of chloroform and 30 ml of water were added to the residue. The organic layer was separated, washed with five 60-ml portions of water, dried over sodium sulfate, filtered and concentrated under reduced pressure. The residue was distilled (bath temperature 190°–210°, 0.1mm), the distillate was dissolved in ether and hydrogen chloride gas passed into the solution to give 0.9g of white precipitate. The precipitate was collected by suction filtration and recrystallized from methanol-acetone: m.p. 275°–278° (d);

IR (nujol) 2680 (m), 2560(m), 2500 (m), 2460 (m) cm$^{-1}$;

NMR(D$_2$O) δ 1.4–3.5 (14H, m, aliphatic), 7.15 (9H, m, aromatic).

Anal. for C$_{20}$H$_{24}$NCl (313.9): Calculated: C, 76.53; H, 7.70; N, 4.46. Found: C, 76.43; H, 7.93; N, 4.30.

EXAMPLE 7

Preparation of
3-propyl-1,2,3,4,5,6-hexahydro-1,6-methano-3-benzazocine hydrochloride To 1.32 g. (0.00763 mol) of 1,2,3,4,5,6-hexahydro-1,6-methano-3-benzazocine and 2.66g (0.0193 mol) potassium carbonate in 16 ml of dimethylformamide (freshly distilled from calcium hydride) was added 1.36g (0.0080 mol) of propyl iodide. The mixture was stirred and heated at 110° for 2.5 hours, cooled and filtered. The recovered solid was washed with 15 ml of chloroform and the filtrates combined and concentrated under reduced pressure. Distillation of the residue (90°–120° bath temperature, 0.1 mm) gave 0.81g (49%) of free amine. The amine was dissolved in ether, the solution dried over molecular sieves and filtered through Celite. Hydrogen chloride gas was passed into the filtered solution forming a white precipitate. Recrystallization from acetone-ether gave needles melting at 195°–197° :m/e 215 (M+-HCl);

IR(CHCl$_3$) 2700–2300 broad (s), 1480 (s), 1450 (s), 1430 (s), 1290–1220 broad (s) cm$^{-1}$;

NMR(D$_2$0) δ0.7–4.0 (17H, m, aliphatic), 7.4 (4H, m, aromatic).

Anal. for C$_{15}$H$_{22}$NCl·5H$_2$O (260.8): Calculated: C, 69.08 H, 8.89; N, 5.37. Found: C, 69.32; H, 9.22; N, 5.32.

EXAMPLE 8

Preparation of
3-allyl-1,2,3,4,5,6-hexahydro-1,6-methano-3-benzazocine hydrochloride To 2.00g (0.0116 mol) of 1,2,3,4,5,6-hexahydro-1,6-methano-3-benzazocine and 2.88 g (0.034 mol) of sodium bicarbonate in 60 ml of absolute ethanol was added 1.4 g (0.0116 mol) 3-bromopropene. The mixture was stirred at reflux for 19 hours, cooled, filtered and the filterpad washed with 20 ml of ethanol. The combined filtrates were concentrated in vacuo to leave a residue which was triturated with acetone-ether, filtered through Celite and the filtrate concentrated under reduced pressure. Distillation of the residue (118°–125° bath temperature, 0.15 mm) gave 1.35g (55%) of amine. The amine was dissolved in ether, the ethereal solution dried over molecular sieves, filtered and hydrogen chloride passed into it to give a copious white precipitate. The solid was filtered and recrystallized from acetone-ether: m.p. 214°–216° (d); m/e 213 (M+-HCl);

IR(CH$_2$Cl$_2$) 2600–2200 broad (s), 1480 (m), 1460 (m), 1420 (m) cm$^{-1}$;

NMR(D$_2$O) δ2.0–4.0 (12H, m, aliphatic), 5.4–6.2 (3H, m, vinylic), 7.4 (4H, m, aliphatic).

Anal. for C$_{15}$H$_{20}$NCl (249.8): Calculated: C, 72.13; H, 8.07; N, 5.61. Found: C, 72.16; H, 8.30; N, 5.50.

EXAMPLE 9

Tests for Pharmaceutical Activity

A series of compounds according to Formula I (racemic mixtures) was selected to establish pharmaceutical property boundary conditions rather than merely attempting to prepare the potentially most analgesically active compounds of this ring system (e.g., with one or more of the following definitions: R$_1$ = hydroxy or methoxy; R$_4$ = other than hydrogen; R$_5$ = methyl; at least one of R$_6$ and R$_7$ = methyl or ethyl). For establishing whether (a) Analgesic activity would be present in the parent and N-methyl derivatives without concomitant physical dependence liability;

(b) The N-phenylethyl derivative would show useful analgesic activity, little or no physical dependence liability and no antagonist activity; and (c) The presence of certain N-substituents would confer antagonist activity on members of this new ring system, Tests for analgesic activity were conducted using intravenous administration in the reliable Eddy mouse hot plate assay described in J. Pharmacol. Exp. Ther. 17:385 (1953). The results are set forth in Table 1, together with the activities of morphine and codeine reported as evaluation standards.

ing Single Dose Suppression (SDS) data monkeys, physically dependent on 3.0 mg/kg of morphine sulfte q6H, were withdrawn until abstinence signs of intermediate severity were present (12–14 hours). The coded drug was injected at this time by persons other than the observer. The monkeys were graded just prior to injection and at intervals of ½, 1, 2, 3, 4, 5 and 6 hours after injection. Grades were based on withdrawal intensity or opiate-like depression and side effects, if present. The results are shown in Tables 2 through 5 together with evaluations thereof by Dr. Henry H. Swain at the University of Michigan. Dosages are in mg/kg.

Non-withdrawn, morphine dependent monkeys were also administered Compounds A and B in an attempt to precipitate the morphine abstinance syndrome; no such result was observed, indicating that these compounds are not morphine antagonists.

Normal monkeys (not dependent on morphine) were also injected with Compounds A and B in an attempt to elicit the narcotic syndrome; no obvious narcotic signs were observed.

The compounds of Formula I thus appear to have an unusual combination of properties in that they are strong analgesics without significant physical dependence liability or narcotic antagonist properties. The separation of the last from the first two properties is quite unexpected in comparison with known compounds and advantageous in that narcotic antagonist properties are generally accompanied by psychotomimetic effects in man which preclude practical use as analgesic agents.

TABLE 1

| COMPOUND | ED$_{50}$(mg/kg) | onset | (MINUTES) peak | duration |
|---|---|---|---|---|
| A  [structure] NH . HCl | 4.9 (3.6–6.5) | 3.3 | 18.0 | 97.5 |
| B  [structure] NCH$_3$ . HCl | 4.2 (2.6–6.7) | 3.2 | 20.3 | 104 |
| C  [structure] NCH$_2$CH(CH$_2$)(CH$_2$) . HCl | 3/10 at 20 mg/kg & 4/10 at 50 mg/kg | Caused convulsions. | | |
| D  [structure] NCH$_2$CH$_2$C$_6$H$_5$ . HCl | 8.8 (6.2–12.5) | 4.7 | 25.6 | 123 |
| E  [structure] NCH$_2$CH$_2$CH$_3$ . HCl | 16.2 (11.7–22.4) | 3.6 | 32.1 | 120 |
| F  [structure] NCH$_2$CH=CH$_2$ . HCl | 19.4 (13.1–28.7) | 3.2 | 16.3 | 119 |
| morphine | 1.2 (0.9–1.3) | | | |
| codeine | 7.5 (6.8–8.3) | | | |

EXAMPLE 10

Physical Dependence Liability Testing

Physical Dependence Liability testing was conducted on Compounds A, B, C and F of Table 1. For determin-

TABLE 2
COMPOUND A

| Doses Tested: | No. of Monkeys | Type of Experiment* | Effects: |
|---|---|---|---|
| 2.0 | 2 | SDS | No apparent effect |
| 4.0 | 2 | SDS | Apparent increase in severity of abstinence signs |
| 8.0 | 2 | SDS | Apparent increase in severity of abstinence signs |
| 4.0 | 2 | NW* | No precipitation of abstinence signs. Animals showed a slight increase in respiration and slight guarding of the abdomen. |
| 8.0 | 2 | Normals | No obvious narcotic signs. The animals showed piloerection, a mild increase in respiration, appeared to be apprehensive and were aggressive when handled. |

SDS-Single Dose Suppression (definitive quantitative assay)
NW*-Attempted precipitation of abstinence in non-withdrawn, morphine-dependent monkey.
Estimated Physical Dependence Capacity: Not morphine-like.
Duration of Drug Action: Unknown
Dose estimated to be equivalent to 3.0 mg/kg of morphine sulfate: Not morphine-like.

TABLE 3
COMPOUND B

| Doses Tested: | No. of Monkeys | Type of Experiment* | Effects: |
|---|---|---|---|
| 2.0 | 2 | SDS | No apparent effect |
| 4.0 | 2 | SDS | No obvious effect; more retching and vomiting than would be expected in withdrawing monkeys. |
| 4.0 | 2 | NW* | No obvious effect; slight retching and vomiting |
| 8.0 | 2 | NW | No obvious effect; possibly a slight degree of muscle relation and body sag |
| 8.0 | 2 | Normals | For the first 10 minutes, there was slight stimulation (lip smacking, facial redness, increased respiration); thereafter only slight muscle weakness decreased movement and a general impression of malaise |

*NW-Attempted precipitation of abstinence in non-withdrawn, morphine-dependent monkeys.
SDS-Single Dose Suppression (Definitive quantitative assay)
Estimated Physical Dependence Capacity: Little or none at doses tested.
Duration of Drug Action: Unknown
Dose estimated to be equivalent to 3.0 mg/kg of morphine sulfate: No morphine-like effects seen.
Remarks:
In the doses tested, this drug neither suppressed nor precipitated the signs of morphine abstinence; its direct effects were not striking but the animals seemed somewhat nauseated and generally unhappy.

TABLE 4
COMPOUND C

| Doses Tested | No. of Monkeys | Type of Experiment* | Effects: |
|---|---|---|---|
| 5.0 mg/kg | 2 | SDS | No obvious effect |
| 10.0 mg/kg | 2 | SDS | No obvious effect |
| 20.0 mg/kg | 2 | SDS | One of the two animals convulsed four minutes after the injection, and the other appeared preconvulsive for the first 30 minutes after receiving the drug. There was no effect upon the progression of the abstincence signs. |

SDS - Single Dose Suppression (Definitive quantitative assay)
Estimated Physical Dependence Capacity: None
Duration of Drug Action: Unknown
Dose estimated to be equivalent to 3.0 mg/kg of morphine sulfate: Not morphine-like
Remarks:
The drug causes convulsions at a dose which neither suppresses nor precipitates abstinence.

TABLE 5
COMPOUND F

| Doses Tested: | No. of Monkeys | Type of Experiment* | Effects: |
|---|---|---|---|
| 1.0 | 2 | SDS | No apparent effect |
| 2.0 | 2 | SDS | No apparent effect |
| 4.0 | 2 | SDS | No apparent effect |
| 8.0 | 2 | SDS | No apparent effect |
| 16.0 | 2 | SDS | No obvious effect; the drug may produce a little CNS depression, but there is no effect upon the progression of abstinence signs. |
| 32.0 | 2 | SDS | The animals convulsed at 4 and 6 minutes respectively after the injection of this dose of the drug. |

SDS-Single Dose Suppression (Definitive quantitative assay)
Estimated Physical Dependence Capacity: None
Duration of Drug Action: Unknown
Dose estimated to be equivalent to 3.0 mg./kg. of morphine sulfate: Unknown
Remarks:
At doses smaller than that which produced convulsions, this drug had little if any effect upon the animals and the development of the abstinence syndrome.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound having in the free base form the formula

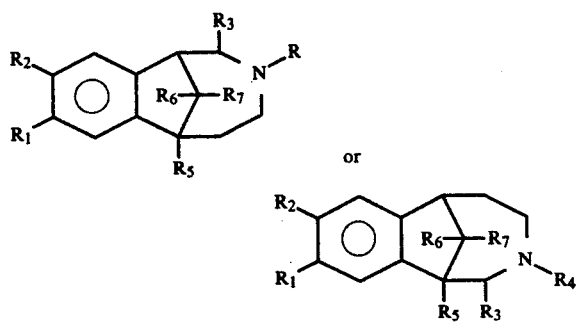

wherein
R₁ and R₂ are each hydrogen, halogen or non-sterically hindered alkyl of 1-6 carbon atoms, hydroxy, alkoxy of 1-6 carbon atoms, alkanoyl or alkanoyloxy of 2-7 carbon atoms, amino, mono- or dialkylamino wherein each alkyl is of up to 4 carbon atoms and each alkyl is unsubstituted or monosubstituted by hydroxy, chlorine, bromine, trifluoromethyl or amino; or R₁ and R₂ collectively are methylenedioxy or ethylenedioxy;

R₃ is hydrogen or alkoxy of 1-6 carbon atoms;

R₄ is hydrogen, alkyl, alkenyl or alkynyl of up to 6 carbon atoms, cycloalkyl, cycloalkylalkyl, cycloalkylalkenyl, cycloalkenyl or cycloalkenylalkyl, with 3 or 4 carbon atoms in the cyclic group of each, phenyl alkyl or phenylalkenyl of up to 9 carbon atoms which is unsubstituted or monosubstituted by amino alkylamino or dialkylamino each of up to 8 carbon atoms, carbalkoxy, alkoxy, alkanoyl or alkanoyloxy of 1-4 carbon atoms, or by chlorine, bromine, trifluoromethyl cyano or hydroxy;

R₅ is hydrogen, alkyl, alkoxy, alkanoyl or alkanoyloxy of 1-6 carbon atoms, hydrocarbon aryl, alkaryl of 6 or 10 ring carbon atoms and 1-4 alkyl carbon atoms optionally monosubstituted by hydroxy, chlorine, bromine, trifluoromethyl or amino; and one of R₆ and R₇ is hydrogen, hydroxy, alkyl or alkoxy of 1-4 carbon atoms and the other of R₆ and R₇ is hydrogen, hydroxy, alkyl or alkoxy of 1-6 carbon atoms, hydrocarbon aryl, alkaryl or aralkyl of 6 or 10 ring carbon atoms and 1-4 alkyl carbon atoms, each of which is optionally substituted by 1-3 of hydroxy, halogen or amino.

2. A compound according to claim 1, wherein R₁ is hydroxy, alkoxy, alkanoyl or alkanoyloxy each of 1-4 carbon atoms.

3. A compound according to claim 1, wherein R₃ is hydrogen or alkoxy of 1-3 carbon atoms.

4. A compound according to claim 1, wherein R₄ is hydrogen, alkyl, alkenyl, cycloalkyl, cycloalkylalkyl, cycloalkylalkenyl, cycloalkenyl, cycloalkenylalkyl, phenyl, phenylalkyl, benzyl or benzalkyl.

5. A compound according to claim 1, wherein R₄ is methyl, allyl, dimethylallyl, 2-phenylethyl, cyclobutylmethyl or cyclopropylmethyl.

6. A compound according to claim 1, wherein R₅ is hydrogen, alkyl, alkoxy, alkanoyloxy or carboalkoxy ester of 1-4 carbon atoms, phenyl or benzyl.

7. A compound according to claim 1, wherein R₅ is hydrogen, methyl, phenyl or acetoxy.

8. A compound according to claim 1, wherein one of R₆ and R₇ is hydrogen and the other of R₆ and R₇ is hydrogen, hydroxy, alkyl or alkoxy of 1-3 carbon atoms.

9. A compound according to claim 1, wherein one of R₆ and R₇ is phenyl, tolyl or benzyl.

10. A compound according to claim 1, wherein one of R₆ and R₇ is H and the other and R₅ are alkyl of 2-5 total carbon atoms.

11. A compound according to claim 1, wherein one of R₆ or R₇ is H while the other and R₅ and R₄ have alkyl groups, the total number of carbon atoms at the three alkylated positions being 3-7.

12. A compound according to claim 1, wherein R₁ is hydroxy or acetyl.

13. A compound according to claim 1, wherein R₂ is hydrogen.

14. A compound according to claim 1, wherein R₃ is hydrogen.

15. A compound according to claim 1, wherein R₁ is hydroxy, alkoxy, alkanoyl or alkanoyloxy of 1-4 carbon atoms; R₂ is hydrogen; R₃ is hydrogen, alkyl or alkoxy of 1-3 carbon atoms; R₄ is methyl, alkyl, dimethylalkyl, 2-phenylethyl, cyclobutylmethyl or cyclopropylmethyl; R₅ is hydrogen, alkyl, alkoxy, alkanoyloxy or a carboalkoxy ester of 1-4 carbon atoms, phenyl or benzyl; and one of R₆ and R₇ is hydrogen and the other of R₆ and R₇ is hydrogen, hydroxy, alkyl or alkoxy of 1-3 carbon atoms.

16. A pharmaceutical composition suitable for use in treating the nociceptive effect in a living animal, comprising an analgesically effective amount of a compound according to claim 1 in combination with a pharmaceutically acceptable carrier.

17. A process for alleviating pain in a living animal, which comprises administering a safe and analgesically effective amount of a compound according to claim 1 to a mammal afflicted therewith.

* * * * *

UNITED STATES PATENT OFFICE
CERTIFICATE OF CORRECTION

PATENT NO. : 4,165,371
DATED : August 21, 1979
INVENTOR(S) : Mazzocchi et al.

It is certified that error appears in the above-identified patent and that said Letters Patent are hereby corrected as shown below:

Column 1, lines 6-8: Please change the first sentence to read as follows: --- The invention described herein was made in the course of work conducted under a grant or award from the United States Department of Health and Human Services. ---

Signed and Sealed this

Eleventh Day of November 1980

[SEAL]

Attest:

SIDNEY A. DIAMOND

Attesting Officer          Commissioner of Patents and Trademarks